United States Patent

Brumbach

[11] Patent Number: 5,562,610
[45] Date of Patent: Oct. 8, 1996

[54] NEEDLE FOR ULTRASONIC SURGICAL PROBE

[75] Inventor: Joseph F. Brumbach, Niles, Ill.

[73] Assignee: FibraSonics Inc., Chicago, Ill.

[21] Appl. No.: 319,727

[22] Filed: Oct. 7, 1994

[51] Int. Cl.$^6$ ................................................. A61B 17/20
[52] U.S. Cl. ......................... 604/22; 604/266; 604/268; 604/272; 606/169; 607/97
[58] Field of Search .......................... 128/200.16, 763; 433/119; 604/22, 35, 36, 43, 44, 156, 264, 266, 268, 272, 274, 118, 119, 902; 606/167, 169, 170, 171, 185, 189; 607/97

[56] References Cited

U.S. PATENT DOCUMENTS

| | | |
|---|---|---|
| 2,227,727 | 1/1941 | Leggiadro . |
| 3,542,031 | 11/1970 | Taylor . |
| 3,589,363 | 6/1971 | Banko . |
| 3,732,858 | 5/1973 | Banko . |
| 3,805,787 | 4/1974 | Banko . |
| 3,823,717 | 7/1974 | Pohlman et al. .................... 604/22 X |
| 3,844,272 | 10/1974 | Banko . |
| 3,896,811 | 7/1975 | Storz . |
| 3,930,505 | 1/1976 | Wallach . |
| 3,990,452 | 11/1976 | Murry et al. . |
| 3,996,935 | 12/1976 | Banko . |
| 4,061,146 | 12/1977 | Baehr et al. . |
| 4,493,694 | 1/1985 | Wuchinich .......................... 604/22 |
| 4,516,398 | 5/1985 | Wuchinich . |
| 4,660,573 | 4/1987 | Brumbach . |
| 4,689,040 | 8/1987 | Thompson ........................ 604/22 |
| 4,921,476 | 5/1990 | Wuchinich . |
| 5,151,083 | 9/1992 | Pichler ............................ 604/22 |
| 5,178,605 | 1/1993 | Imonti ............................ 604/22 |
| 5,248,297 | 9/1993 | Takase ........................... 604/22 |
| 5,254,082 | 10/1993 | Takase . |
| 5,286,256 | 2/1994 | Mackool ......................... 604/22 |
| 5,391,144 | 2/1995 | Sakurai et al. ................... 604/22 |

Primary Examiner—Corrine M. McDermott
Assistant Examiner—N. Kent Gring
Attorney, Agent, or Firm—Welsh & Katz, Ltd.

[57] ABSTRACT

A hollow operating needle for an ultrasonic surgical probe for fragmenting and removing material from the body has an elongated tapered portion which is coupled at its larger end portion to an ultrasonic motor for receiving and transmitting vibrations along the length of the needle to the operating end of the needle, with the needle defining at least one generally rectangular opening extending co-axially from the operating tip end and having the intersections of the longer sides of the at least one opening and the operating tip end being beveled, whereby a substantial portion of irrigating fluid supplied adjacent the operating end portion of the needle reaches the operating tip end of the needle and the surgical site and another substantial portion of the fluid passes through the at least one opening without reaching the operating tip of the needle. A generally concentrically positioned sleeve positioned about the needle extending from a housing enclosing the ultrasonic motor, thereby forming an annular passage with the needle through which irrigating fluid can be passed and can exit the annular passage adjacent the operating tip end portion of the needle.

9 Claims, 2 Drawing Sheets

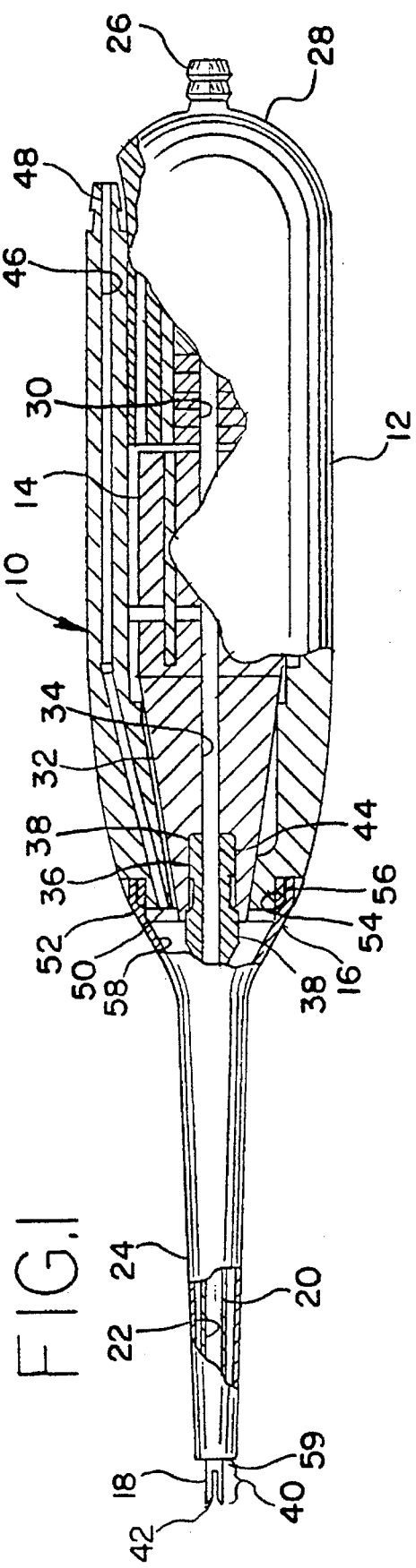
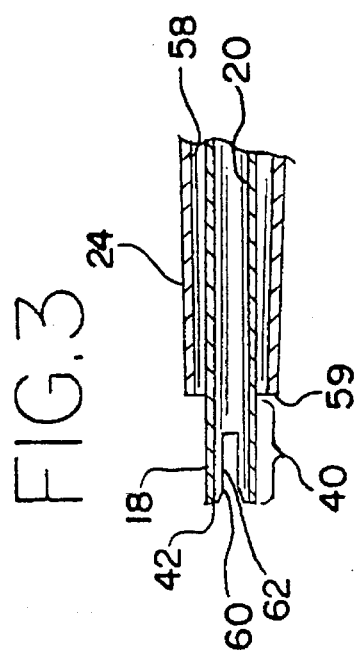
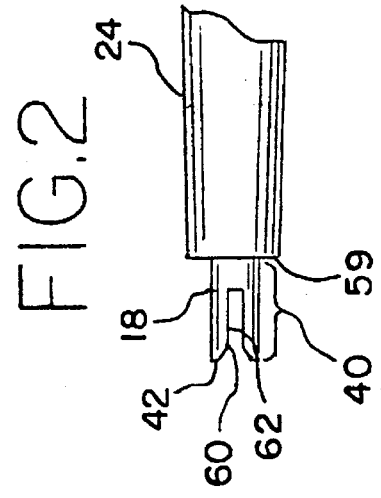

NEEDLE FOR ULTRASONIC SURGICAL PROBE

BACKGROUND OF THE INVENTION

1. Field of the Invention

The present invention relates to an ultrasonic surgical probe or scalpel for use in the removal of inorganic or organic tissue from a living body, and, more particularly, to a needle for an ultrasonic surgical tool capable of imparting ultrasonic vibrations to tissue and calculi in a living body, such as a tumor, cataract or stone, to fragment the tissue, or calculi, particularly in the renal system and gall bladder, and of removing fragmented tissue and fluids from the surgical site, and for other applications including ophthalmic applications.

2. Description of Related Art

Ultrasonic probes or scalpels for the fragmentation and removal of inorganic materials and fluids from living beings are known to the art. For example, U.S. Pat. No. 2,227,727, issued Jan. 7, 1941 to Vincent Leggiardro, discloses an apparatus for fragmenting naturally formed stones, such as bladder stones, kidney stones, and the like, utilizing a high speed reciprocating rod which may have a blunt end, a sharp or chisel point end, a cutting blade, or combinations thereof, such as a cutting blade having a blunt end.

While the apparatus disclosed in U.S. Pat. No. 2,227,727 involved a two part housing, with the sonic transducer in one part and the reciprocating rod in another part, in later apparatus the transducer and probe were connected together to form a unitary instrument. In U.S. Pat. No. 3,896,811, issued Jul. 29, 1975 to Karl Storz, the transducer and rod-like probe are coupled and both are enveloped by a jacket providing an air gap and preventing the sides of the probe from contacting the body except at its end. Furthermore, the probe may have a scalloped end to effect the dissolution or break-up of stones.

An improvement in such instruments is disclosed in U.S. Pat. No. 3,990,452, issued Nov. 9, 1976 to Edward J. Murry and Joseph F. Brumbach, which also reviews a number of articles relating to the development of ultrasonics in medicine and, particularly for use in cataract surgery, and notes the incorporation of irrigation and aspiration with ultrasonics.

A particular arrangement in an ultrasonically vibrated surgical tool using an irrigation fluid and an anti-coagulant, is disclosed in U.S. Pat. No. 4,493,694, issued Jan. 15, 1985 to David G. Wuchinich. The arrangement utilizes a hollow tool having a suction passage and at least one pre-aspirating orifice in the wall of the tool, and a sleeve concentrically spaced about the tool for admitting fluid from a supply into the space between the sleeve and the tool and passing substantially all of the fluid through the pre-aspirating orifice.

Although the arrangement of having substantially all of the fluid pass through the pre-aspirating orifice as in U.S. Pat. No. 4,493,694, may be useful in some operations, it is often preferable to have a substantial portion of the irrigating fluid flow to or spray the surgical site to assist in washing the fragmented material or tissue and any excess blood from the site into the end of the tool assisted by suction. In the arrangement where a substantial portion of the irrigating fluid desirably flows to or is sprayed on the surgical site, an anticoagulant is not employed as such an additive may cause excessive bleeding at the site. In one commercial ultrasonic probe, a shorter sleeve is employed, such that the open end of the sleeve does not cover the preaspiration orifice, and no anticoagulant is used, and thereby the surgical site is irrigated to assist the removal of material from the site without causing excessive bleeding due to an anticoagulant.

However, none of these arrangements are completely satisfactory, particularly where the volume of irrigation and other conditions of operation of the tool varies as selected by the surgeon and with the surgical procedure. Therefore, there is a need for an improved ultrasonic surgical tool construction which provides for improved fragmentation of tissue and accretions, and which can provide for a consistent, substantial flow of irrigation fluid at the operating end of the tool under various operating parameters, while providing improved operation of the tool.

SUMMARY OF THE INVENTION

Hence, it is one object of the present invention to provide an improved needle for an ultrasonic surgical probe.

It is another object of the present invention to provide an improved needle for an ultrasonic surgical probe wherein a means is provided for consistently assuring a substantial portion of the fluid supplied to the probe will be applied to the surgical site which assurance is not dependent on the amount of fluid and suction supplied to the probe.

It is still another object of the present invention to provide an improved needle for an ultrasonic surgical probe having means for consistently assuring a substantial portion of the fluid supplied to the probe will be applied to the surgical site and a portion of the fluid is provided to the suction path of the probe without reaching the surgical site.

These and other objects and advantages of the present invention will be apparent from the following description considered in conjunction with the accompanying drawings.

In accordance with the present invention there is provided an improved needle for an ultrasonic surgical probe for fragmenting and removing material from the body in which the probe includes a handpiece containing an ultrasonic motor capable of generating ultrasonic vibrations, the hollow operating needle being tapered and extending from its larger end outwardly from the handpiece and having an operating end portion at its smaller, opposite end defining at least one opening extending from the tip end portion of the needle toward the larger end, i.e., toward the handpiece, the needle being coupled to the motor to receive and transmit ultrasonic vibrations therefrom along the length of the needle. Optionally, a sleeve can be positioned about the needle extending from the handpiece toward, but less than the full distance to the operating end of the needle. The sleeve, if used and the needle define an open ended annular space for the passage of fluid supplied to the handpiece through the annular space. The handpiece further includes means for connecting the hollow operating needle to a source of suction such that suction can be applied to cause material to be drawn into the end of the needle and to pass through the hollow portion of the needle. The handpiece may also include means for connecting the handpiece to a source of fluid, particularly where a sleeve as noted above is used, such that fluid can flow through the annular space between the operating needle and the sleeve and exit from the open end of the annular space.

The improved needle of this invention, during its operation with ultrasonic vibrations being generated by the motor in the handpiece and transmitted to the operating end of the needle, with suction applied to the hollow portion to the needle to draw material therethrough and with a sleeve as described above and with fluid supplied to the annular space defined by the sleeve and the needle, results in a substantial portion of the fluid exiting the annular open end of the sleeve reaching the operating end of the needle and hence the surgical site, and another substantial portion of the fluid passing through the at least one opening defined in the tip end portion of the needle for passage through the hollow needle without reaching the operating end of the needle and the surgical site. In this manner the surgical site is irrigated by a substantial portion of the fluid supplied to the handpiece to irrigate the site and to assist the flow of the fluid, blood and tissue or other matter separated from the tumor or calculi or other mass of the patient's body by the operating end of the needle of the probe into the end of the needle and the hollow passage therein and through the handpiece to means for collecting the material. Further in this manner, another substantial portion of fluid supplied to the handpiece passes through the at least one opening in the tip end portion of the needle to cool the needle and ultrasonic motor and to maintain the suction and the flow of material removed from the surgical site through the needle and handpiece in the event the end of the needle is obstructed such as by being temporarily pushed against the tumor or other mass.

In accordance with this invention, the at least one opening in the tip end portion of the operating needle is generally rectangular and extends coaxially from the operating end of the needle. The needle of the present invention preferably comprises two tip end openings or may comprise three or more openings, limited only by the strength and/or integrity of the needle material, preferably titanium or an alloy of titanium defining the needle tip portion. Preferably the at least one tip end opening in the needle operating end portion is a modification of a rectangular opening, namely by having the intersections of the longer, co-axial sides of the generally rectangularly opening and the operating tip end beveled, and preferably the intersections are beveled at an acute angle, and most preferably at an angle of about from 30 to about degrees to the co-axial side of the opening. Additionally, it is preferred to have the closed end of the opening or openings i.e., side of the opening which is transverse to the axis of the needle, being rounded or arcuate.

Unexpectedly, it has been found that through the use of the needle of the present invention considerably more material can be removed from test tissue-masses as compared to probes under the same operating conditions using pre-aspirating orifices as heretofore described. It has further been unexpectedly found that a wider range of tissue can be fragmented and removed than could be fragmented and removed with the heretofore described probes having pre-aspirating orifices in the needle of the probe spaced from the tip end.

BRIEF DESCRIPTION OF THE DRAWINGS

FIG. 1 is a side view, partially in cross-section, showing schematically, a needle of the present invention installed on an ultrasonic surgical probe.

FIG. 2 is an enlarged view of a portion of FIG. 1 showing details of the preferred embodiment of the present invention.

FIG. 3 is enlarged sectional view of the embodiment of the invention as shown in FIG. 2.

DESCRIPTION OF THE PREFERRED EMBODIMENTS

Figure 4:
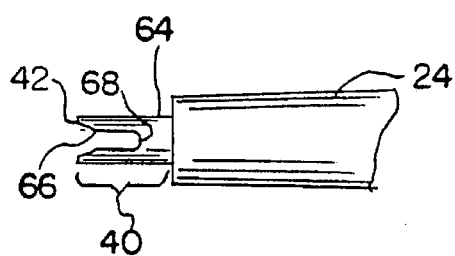
FIG. 4 is a view identical to FIG. 2 of a modification of the embodiment of the invention as shown in FIGS. 1–3.

In the preferred embodiments of the present invention, which are schematically illustrated in FIG. 1, an ultrasonic surgical probe is generally referenced by numeral 10. A handpiece housing or casing 12, which preferably is of non-conducting material, such as a polymer, encloses an ultrasonic motor 14. Extending outwardly from one end 16 of housing 12 is an operating needle 18 of the present invention having an elongated tapered body 20 defining an axial bore 22 extending from one end of the needle to the other. In the preferred embodiments a sleeve 24 is generally concentrically positioned about and spaced from needle 18. Sleeve 24 may be a single molded piece as shown, or may comprise two or more sections glued or otherwise secured together, with the several sections of polymers of different properties, e.g. one part relatively rigid and another part relatively flexible. A power source (not shown) is connected to ultrasonic motor 14, which may be a known type of ultrasonic motor, such as an ultrasonic transducer with piezoelectric crystals or a magneto-strictive transducer which may be electromagnetically excited, but preferably is the former. Power can be applied to motor 14 through electrical conductors led through suitable openings (not shown) in housing 12.

In the preferred embodiments, housing 12 further includes a nipple 26 at its rear end 28 opposite end 16 supporting needle 18 and sleeve 24, to which is connected a suction or aspiration source (not shown). Extending generally axially through housing 12 and ultrasonic motor 14 is a suction or aspiration passage 30 which is coupled to nipple 26 and to bore 22 of needle 18 so that upon suction applied at nipple 26, suction is applied through passage 30 and bore 22 of needle 18. Housing 12, in the embodiments illustrated in FIG. 1, also encloses a motor 14 and horn 32 which is coupled to needle 18 and which is capable of transmitting ultrasonic vibrations from motor 14 to needle 18. Horn 32 has an axial hollow bore 34, which constitutes a portion of suction passage 30. Horn 32 at its end has an axial recess 36 which is internally threaded.

Tapered body 20 of operating needle 18 has an enlarged or larger end portion 38 and an operating end portion 40 opposite end portion 38 which terminates in an operating tip end 42. Larger end portion 38 has an externally threaded portion 44 extending therefrom so as to be securely but releasably threadedly mounted in the recess 36 of horn 32. Bore 22 of needle 18 extends through portion 44 and permits suction applied through passage 30 to be applied therethrough.

In the preferred embodiments where a sleeve 24 as defined herein is used, housing 12 further includes an irrigating fluid passage 46 formed therein, and a nipple 48 located near rear end 28 to which a supply of fluid (not shown) can be connected. Irrigating passage 46 extends through housing 12 and exits housing 12 at port 50. Sleeve 24 has a flared end portion 52 having internal threads 54 in the substantially cylindrical end portion thereof which engage external threads 56 on end 16 of housing 12 so as to be securely, but releasably threadedly mounted to housing 12. When sleeve 24 is securely mounted on housing 12, irrigation passage 46 is in communication with the annular space 58 defined between sleeve 24 and needle 18 through port 50 to permit fluid supplied to nipple 48 to flow through passage 46, port 50 and annular space 58 to the open end 59 of sleeve 24.

In the preferred embodiment shown schematically in FIG. 1, and more particularly in FIGS. 2 and 3, needle 18 in tip end portion 40 extending rearwardly from tip end 42, includes a pair of spaced apart tip end openings or slots 60, which in the embodiment shown, are generally rectangular longitudinally, i.e., coaxially, directed. Although a pair of slots 60 is shown, one or a larger number of slots can be employed, for example three or four. As shown in the drawing, slots 60 defined in portion 40 extend from tip end 42 a short distance substantially less than the distance to larger end portion. The longer sides 62 of slots 60 are coaxial with the elongation of body 20 and have their intersections with operating tip end 42 beveled. It is preferred that the intersections of sides 62 and tip end 42 be beveled at an acute angle and most preferably at an angle of from about 30 degrees to about 60 degrees to the sides 62.

Although the preferred needle material is titanium or an alloy of titanium, and is not considered brittle even with the transmission of ultrasonic vibrations during the operation of the probe, the preferred embodiment of this invention thus described substantially reduces or eliminates the breaking off of small pieces during extreme conditions of longer use than would be encountered in expected surgical procedures.

Figure 5:
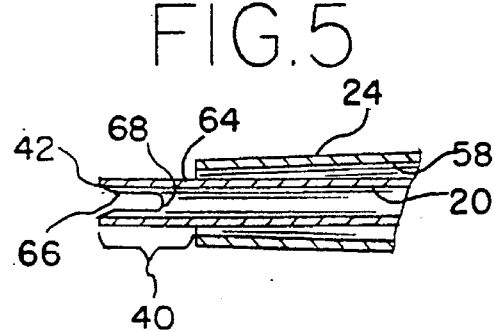
FIG. 5 is a view identical to FIG. 3 showing the modification illustrated in FIG. 4.

Another preferred embodiment of the present invention is illustrated in FIGS. 4 and 5, which is schematically generally shown in FIG. 1, and wherein components which are common to the first described preferred embodiments have the same reference numerals as in FIGS. 1–3. In this embodiment, needle 64 in the tip end portion 40 thereof extending co-axially from its operating tip end 42 toward housing 12, has a pair of slots 66 which are generally rectangular and has beveled corners at their intersections with tip end 42, as in the embodiment shown in FIGS. 2 and 3, but the closed ends 68 of slots 66 are rounded or arcuate, thus eliminating the internal corners of the slots 60 in the earlier described embodiment.

In the preferred embodiments of the present invention, sleeve 24 extends toward the spaced apart slots 60, 66 with its open end terminating short of the spaced apart slots, i.e. terminating at a distance from housing 12 less than the distance from the housing to the spaced apart slots. It is also preferred in the embodiments of this invention that each of the spaced tip end apart slots defined by the needle extends axially from the operating tip end of the needle toward handpiece housing 12 a distance, i.e., the depth of the slots, in the order of 0.1 inch and that the slots have a width in the order of 0.01 inch. It is particularly preferred that the open end of sleeve 24 terminate in the order of from 0.03 to 0.1 inch from the closed end of slots 60, 66. In this manner, during operation of the probe, a substantial portion of fluid passing through irrigating fluid passage 46 and exiting the open end of the annular space 58 between the needle and sleeve 24, reaches the operating end of the needle, and hence the surgical site; while another substantial portion of the fluid exiting the open end of annular space 58 passes through the slots 60, 66 and into bore 22 of the needle and suction passage 30 to ensure the continuous flow of fluid therethrough to improve aspiration of particles, even if the end of the needle is temporarily blocked.

Figure 6:
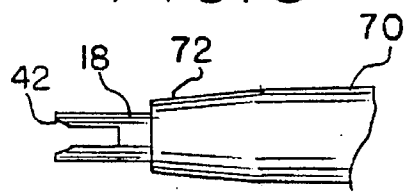
FIG. 6 is a view identical to FIG. 2 showing another embodiment of the invention.
Figure 7:
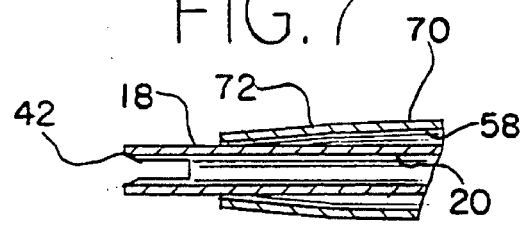
FIG. 7 is a view identical to FIG. 3 showing the embodiment of the invention illustrated in FIG. 6.

Another embodiment of the present invention is shown in FIGS. 6 and 7, wherein the sleeve 70 includes a tapered portion 72, which provides a greater field of vision of the operating tip end 42 of needle 18 during operation of the probe. This embodiment, i.e. providing a tapered portion 72 to the sleeve is applicable to each of the embodiments shown and described herein, and further permits sleeve 70 to have a substantially cylindrical main portion between tapered portion 72 and the flared end portion 52 of the sleeve.

While a particular embodiment of the needle for ultrasonic probe of the invention has been shown and described, it will be appreciated by those skilled in the art that changes and modifications may be made thereto without departing from the invention in its broader aspects and as set forth in the following claims.

What is claimed is:

1. A hollow operating needle for an ultrasonic surgical probe handpiece and adapted to extend therefrom, the handpiece having an ultrasonic motor capable of generating ultrasonic vibrations contained therein, having means for connecting the handpiece and needle to a source of suction, having an open-ended sleeve generally concentrically positioned about the needle extending from said handpiece less than the distance that the operating needle extends from the handpiece, the sleeve defining an open-ended annular space with the needle, and having means for connecting the handpiece to a source of fluid such that fluid can flow through the annular space between the needle and the sleeve for exiting from the open end of the annular space defined by the sleeve, the hollow operating needle comprising:

a. an elongated, tapered body having one end thereof larger than the other and defining an elongated hollow bore extending from one end of the tapered body to the other, said body adjacent said larger end defining a larger end portion;

b. means on the larger end portion of said body for coupling the needle to the ultrasonic motor for receiving and transmitting ultrasonic vibrations from the motor along the length of the needle;

c. said tapered, hollow body terminating in an operating tip end at its end opposite the larger end portion and defining an operating tip end portion; and d. said operating needle defining at least one rectangular opening in the operating tip end portion thereof, said at least one opening defined in said operating tip portion extending from said operating tip end toward said larger end portion a distance substantially less than the distance said hollow body extends from said operating tip end to the larger end portion, with the longer sides of the at least one opening defined in said operating tip end portion being coaxial with the bore defined in the hollow body of the needle and intersecting the operating tip end of the needle, and the intersections of the longer sides of the at least one opening and the said operating tip end being beveled; whereby during operation of the probe a substantial portion of fluid passing through the annular space between said operating needle and exiting therefrom reaches the operating tip end of the needle and another substantial portion of the fluid passes through the at least one opening defined in the operating tip end portion thereof for passage through the bore of the needle without reaching the operating tip end of the needle.

2. The hollow operating needle of claim 1, wherein said needle defines a plurality of spaced apart rectangular openings in the operating tip end portion thereof extending coaxially with said bore defined in the hollow body of the needle from said operating tip end toward said larger end portion a distance substantially less than the distance said hollow body extends from said operating tip end to the larger end, with the longer sides of the plurality of rectangular spaced openings being coaxial with the bore defined in the hollow body of the needle and intersecting the operating tip end of the needle, the intersections of the longer sides of the plurality of the openings and said operating tip end being beveled; whereby during operation of the probe a substantial portion of fluid passing through the annular space between said operating needle and the sleeve and exiting therefrom reaches the operating tip end of the needle and another substantial portion of the fluid passes through the said plurality of openings defined in the operating tip end portion thereof for passage through the bore of the needle without reaching the operating tip end of the needle.

3. The hollow operating needle of claim 1, wherein said needle defines a pair of spaced apart rectangular openings in the operating tip end portion thereof extending coaxially with said bore defined in the hollow body of the needle from said operating tip end toward said larger end portion a distance substantially less than the distance said hollow body extends from said operating tip end to the larger end, with the longer sides of the pair of rectangular shaped openings being coaxial with the bore defined in the hollow body of the needle and intersecting the operating tip end of the needle, and the intersections of the longer sides of the pair of the openings and said operating tip end being beveled; whereby during operation of the probe a substantial portion of fluid passing through the annular space between said operating needle and the sleeve and exiting therefrom reaches the operating tip end of the needle and another substantial portion of the fluid passes through the said pair of openings defined in the operating tip end portion thereof for passage through the bore of the needle without reaching the operating tip end of the needle.

4. The hollow operating needle of claim 3, wherein the intersection of each longer side of the respective opening of the pair of spaced apart openings and said operating tip end is beveled at an acute angle with respect to the respective longer side of the respective opening of the pair of openings in the needle.

5. The hollow operating needle of claim 4, wherein the pair of openings defined by the needle is a pair of equidistantly spaced rectangular openings and wherein the end of each opening closest to the larger end portion of the body and transverse to the bore defined in the hollow body of the needle is arcuate.

6. The hollow operating needle of claim 3, wherein the intersection of each longer side of the respective opening of the pair of spaced apart openings and said operating tip end is beveled at an angle of between about 30 degrees and about 60 degrees to the respective longer side of the respective opening of the pair of openings in the needle.

7. The hollow operating needle of claim 6 wherein the pair of openings defined by the needle extend coaxially with the bore defined by the hollow body from the operating tip end of the needle toward the larger end portion a distance of approximately 0.1 inch.

8. An ultrasonic surgical probe comprising:

a handpiece having an ultrasonic motor contained therein, said motor being capable of generating ultrasonic vibrations;

an operating needle having an elongated, tapered body having one end larger than the other and defining a hollow bore extending from one end of the tapered body to the other and extending outwardly from said handpiece to an operating tip end thereof, and said needle being coupled to said motor for receiving and transmitting ultrasonic vibrations therefrom along the length of said needle to said operating tip end, a portion of said body adjacent said larger end defining a larger end portion and another portion of said body adjacent said operating tip end defining an operating tip end portion;

said handpiece having means for connecting said hollow operating needle to a source of suction such that suction can be applied to cause material to be drawn into the operating tip end of said body of said operating needle and to pass therethrough;

said operating needle defining at least one rectangular opening in the said operating tip end portion extending from the operating tip end thereof toward said handpiece a distance of substantially less than the distance said hollow body extends from the operating tip end of the needle to the handpiece, with the longer sides of the at least one rectangular shaped opening being co-axial with the hollow bore of the needle and intersecting the operating tip end of the needle, and the intersections of the longer sides of the at least one opening and the operating tip end being beveled;

a sleeve generally concentrically positioned about said operating needle and extending from said handpiece toward but less than the distance the needle extends from the handpiece to the at least one rectangular opening in said needle and terminating in an open end, said sleeve defining an open ended annular space with said needle; and said handpiece having means for connecting the handpiece to a source of fluid such that fluid can flow through the annular space between said operating needle and said sleeve for exiting from the open end of the annular space, whereby during operation of the probe a substantial portion of fluid passing through the annular space between said operating needle and said sleeve and exiting therefrom reaches the operating tip end of the needle and another substantial portion of the fluid passes through the at least one opening defined in the needle for passage therethrough without reaching the operating tip end of the needle.

9. An ultrasonic surgical probe comprising:

a handpiece having an ultrasonic motor contained therein, said motor being capable of generating ultrasonic vibrations;

an operating needle having an elongated, tapered body having one end larger than the other and defining a hollow bore extending from one end of the tapered body to the other and extending outwardly from said handpiece to an operating tip end thereof, and said needle being coupled to said motor for receiving and transmitting ultrasonic vibrations therefrom along the length of said needle to said operating tip end, a portion of said body adjacent said larger end defining a larger end portion and another portion of said body adjacent said operating tip end defining an operating tip portion;

said handpiece having means for connecting said hollow operating needle to a source of suction such that suction can be applied to cause fluid and solid material to be drawn into the operating tip end of said body of said operating needle and to pass therethrough;

said operating needle defining a pair of spaced apart rectangular openings in the operating tip end portion extending from the operating tip end thereof toward said handpiece a distance of substantially less than the distance said hollow body extends from the operating tip end of the needle to the handpiece, the longer sides of the rectangular openings being co-axial with the hollow bore of the needle and intersecting the operating tip end of the needle, and the intersections of the longer sides of the pair of openings and the operating tip end being beveled;

a sleeve extending from said handpiece and generally concentrically positioned about said operating needle, said sleeve terminating in an open end defining with said needle an open ended annular space, and said sleeve extending a distance from the handpiece less than the distance from the handpiece to the pair of spaced apart openings in the needle;

said handpiece having means for connecting the handpiece to a source of fluid such that fluid can flow through the annular space between said operating needle and said sleeve for exiting from the open end of the annular space, whereby during operation of the probe a substantial portion of fluid passing through the annular space between said operating needle and said sleeve and exiting therefrom reaches the operating end of the needle and another substantial portion of the fluid passes through the pair of openings defined in the needle for passage therethrough without reaching the operating end of the needle.

* * * * *

UNITED STATES PATENT AND TRADEMARK OFFICE
CERTIFICATE OF CORRECTION

PATENT NO. : 5,562,610
DATED : October 8, 1996
INVENTOR(S) : Joseph F. Brumbach

It is certified that error appears in the above-indentified patent and that said Letters Patent is hereby corrected as shown below:

Column 2, line 56, "Of" should be --of--.

Column 3, line 37, add the angle enumeration --60-- after the phrase "to about".

Claim 2, Column 7, line 6, add --and-- after the comma following "needle".

Signed and Sealed this

Fifteenth Day of July, 1997

Attest:

BRUCE LEHMAN

Attesting Officer

Commissioner of Patents and Trademarks